(12) United States Patent
Erickson et al.

(10) Patent No.: US 7,532,936 B2
(45) Date of Patent: May 12, 2009

(54) PROGRAMMABLE SWITCHING DEVICE FOR IMPLANTABLE DEVICE

(75) Inventors: John H. Erickson, Plano, TX (US); Anthony J. Varrichio, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 475 days.

(21) Appl. No.: 11/109,835

(22) Filed: Apr. 19, 2005

(65) Prior Publication Data

US 2005/0245970 A1 Nov. 3, 2005

Related U.S. Application Data

(60) Provisional application No. 60/563,776, filed on Apr. 20, 2004.

(51) Int. Cl.
*A61N 1/08* (2006.01)
(52) U.S. Cl. ............... 607/48; 607/46; 607/55
(58) Field of Classification Search ............ 607/46, 607/48, 55–57
See application file for complete search history.

(56) References Cited

U.S. PATENT DOCUMENTS

| | | | |
|---|---|---|---|
| 4,428,377 A * | 1/1984 | Zollner et al. | 607/57 |
| 5,603,726 A * | 2/1997 | Schulman et al. | 607/57 |
| 5,674,264 A * | 10/1997 | Carter et al. | 607/57 |
| 6,035,237 A | 3/2000 | Schulman et al. | |
| 6,381,496 B1 * | 4/2002 | Meadows et al. | 607/59 |
| 2002/0095187 A1 * | 7/2002 | Thompson et al. | 607/9 |

FOREIGN PATENT DOCUMENTS

| | | |
|---|---|---|
| WO | WO 02/09808 | 2/2002 |
| WO | WO 02/068046 | 9/2002 |
| WO | WO 03/068068 | 8/2003 |
| WO | WO 2004/012813 | 2/2004 |

OTHER PUBLICATIONS

Gregg Jorgen Suaning; CMOS Neurostimulation ASIC with 100 Channels, Scaleable Output, and Bidirectional Radio-Frequency Telemetry; IEEE Transactions on Biomedical Engineering.

* cited by examiner

*Primary Examiner*—George R Evanisko
*Assistant Examiner*—Joseph M Dietrich
(74) *Attorney, Agent, or Firm*—Christopher S. L. Crawford; Peter Lando; Melissa Acosta

(57) ABSTRACT

A device and method for generating electrical stimulation. The implantable device includes a programmable switching device or array that receives at least one pulse generator output coupled through at least one coupling capacitor. The switching device selectively connects at least one pulse generator output to a plurality of electrode terminals via at least one coupling capacitor. Electrical stimulation signals may be applied directly from the electrode terminals, or are applied through a lead or lead extension having corresponding electrodes electrically connected to the electrode terminals.

8 Claims, 6 Drawing Sheets

PROGRAMMABLE SWITCHING DEVICE FOR IMPLANTABLE DEVICE

CROSS-REFERENCE TO RELATED APPLICATIONS

This application claims priority benefit of U.S. Provisional Patent Application No. 60/563,776 entitled "PROGRAMMABLE SWITCHING DEVICE FOR IMPLANTABLE DEVICE," filed Apr. 20, 2004, the disclosure of which is hereby incorporated herein by reference.

TECHNICAL FIELD

The present invention relates to implantable medical devices, and in particular, to a programmable switching device or array for use in an implantable stimulation device.

BACKGROUND OF THE INVENTION

FIG. 1 illustrates a typical prior art implantable stimulation device. A stimulation source generates one or more electrical signals for delivery of electrical stimulation to a desired location via one or more channels or outputs. The stimulation source produces pulse generator outputs P1, P2, P3, . . . , Pn for delivery to the desired location via output terminals T1, T2, T3, . . . , Tn. As will be appreciated, the term "terminal" as used herein is not limited to an input/output terminal, and also refers to a node or other connection between two or more points or signals, whether internal or external to any integrated circuit or other discrete element(s). The stimulation signals may be applied directly from the output terminals, but are usually applied through a lead or lead extension having corresponding electrodes electrically connected to the output terminals. Any number of the n pulse generator outputs (and corresponding output terminals) may be active or operating at a given time to deliver electrical energy.

Coupling capacitors C1, C2, C3. . . , Cn are provided between each pulse generator output P1 thru Pn and each output terminal T1 thru Tn to block direct current (DC) signals (current, voltage) from being applied to the respective output terminals (and hence to the electrodes of the lead). These capacitors are physically large and require a significant amount of space. In the prior art systems, as the number of pulse generator outputs (and output terminals) operable for stimulation increases (e.g., from 4 to 8, from 8 to 16, 16 to 32, etc.), the number of coupling capacitors also increases—one for each pulse generator output (and output terminal). Increasing the number of outputs and terminals (or electrodes in the lead) allows for increased programmability and selection of stimulation patterns and stimulation points/areas. However, the increase in the number of outputs/terminals also increases the number of large coupling capacitors needed. This is undesirable, as one of the goals is reduce the size of the implantable device.

Accordingly, there is a need for an implantable stimulation device that effectively reduces the number of coupling capacitors that are utilized. In addition, there is needed a programmable switch array or matrix operable for selectively coupling a plurality of generated electrical signals to a plurality of output terminals.

SUMMARY

The present invention is directed to a system and method which, in accordance with one aspect of the present invention, there is provided an implantable device for generating electrical stimulation. The device includes a pulse generator having a plurality of pulse generator outputs and a plurality of coupling capacitors, each of the plurality of capacitors is electrically connected to a respective one the plurality of pulse generator outputs, and a plurality of electrode terminals. A programmable switching device electrically connected to each of the coupling capacitors selectively couples at least one of the plurality of pulse generator outputs to a one of the plurality of electrode terminals, and wherein the number of plurality of electrode terminals is greater than the number of plurality of pulse generator outputs.

In accordance with another aspect of the present invention, there is provided an implantable device as described above wherein the switching device includes means for selectively coupling.

In accordance with one aspect of the present invention, there is provided a method of generating electrical stimulation outputs for stimulating part of a body. A plurality of pulse generator outputs are generated and selectively coupling at least one of the plurality of pulse generator outputs to at least a one of a plurality of electrode terminals, wherein the number of plurality of electrode terminals is greater than the number of plurality of pulse generator outputs.

In accordance with yet another aspect of the present invention, there is provided a system for stimulating a portion of a body. The system includes an implantable device for generating a stimulus, and as described above and herein, and further includes an implantable lead for receiving the stimulus from one or more of the plurality of electrode terminals of the implantable device and applying the stimulus to one or more electrodes.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION OF THE INVENTION

Figure 2:
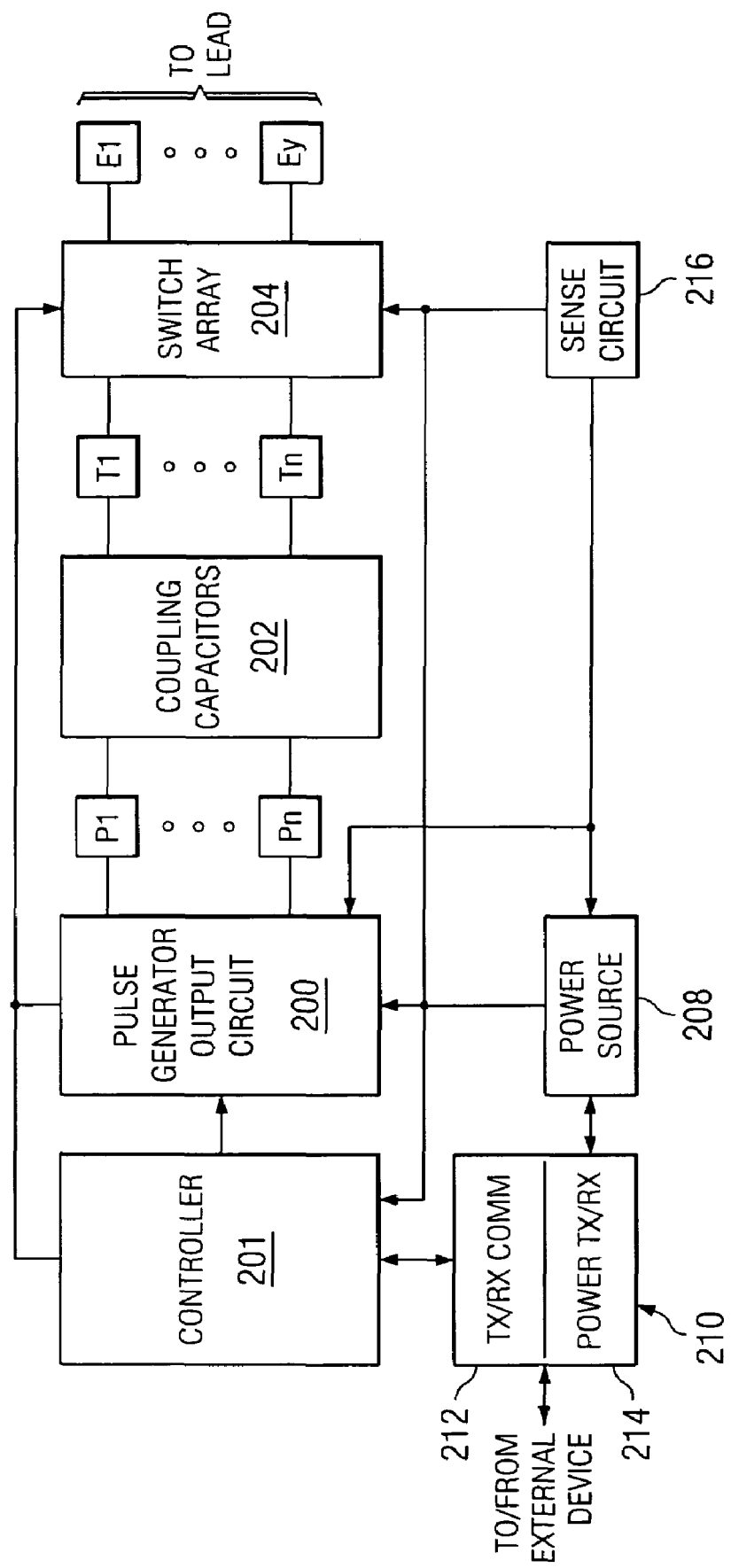
FIG. 2 is a block diagram illustrating an implantable device in accordance with the invention.

Now referring to FIG. 2, there is shown an implantable device (generally, reference numeral 100) having a pulse generator output circuit 200, a controller 201 for generating electrical stimulation signals, coupling capacitors 202, and a switch array (or matrix) 204. The implantable device 100 further includes a power source 208, and a transmitter/receiver 214 for communications with an external device.

The pulse generator output circuit 200 and the controller 201 function together to generate electrical signals (stimulation) for delivery to a desired location. The circuit 200 and controller 201 are shown as separate elements, but their functionality may also be provided by a single element (or multiple elements). As will be appreciated, the controller 201 typically includes a microprocessor or microcontroller and memory. Further, the pulse generator output circuit 201 and controller 200 may include various elements of hardware and/or software.

The pulse generator output circuit 200 and controller 201 function to program, control and generate electrical signals output for stimulation (pulse generator outputs P1 thru Pn). The pulse generator output circuit 200 generates a plurality n of electrical signals via a plurality of separate and independently programmable corresponding terminals P1 thru Pn (referred to herein and hereafter as "pulse generator outputs" or "outputs", and each one may also be referred to as a channel). As readily understood by those skilled in the art, any number of pulse generator outputs may be active at a given time, thus providing a stimulation pattern across the pulse generator outputs, and in many different operational configurations.

Each of the separate pulse generator outputs are programmable and operable to provide an anode state, a cathode state, or a high impedance or off state (i.e., tri-state). As will be appreciated, this would allow each output to be programmed to provide one of a source, sink or high impedance functionality. Such functionality may also operate in accordance with, or similar to, that described in U.S. Pat. No. 4,793,353, which is incorporated herein by reference. It will be understood that such output(s) may mean a fixed anode or cathode, a programmable anode or cathode, or a programmable anode, cathode or high impedance state. Further, such pulse generator output(s) may originate from one or more source circuits, such as separate and independently controllable constant voltage source(s) or constant current source(s), or combination thereof.

Applicants have determined that the typical number of electrodes active at any given period of time of stimulation (stimulation pattern applied to the lead(s)) is generally between two and five. Assuming there exists sixteen operable outputs for stimulation (e.g., sixteen pulse generator outputs for sixteen corresponding electrodes), then during a typical stimulation sequence, between eleven and fourteen of the coupling capacitors are not being utilized at any given time (i.e., providing source/sink functionality). In one embodiment, the present invention provides for a reduction in the number of pulse generator outputs to a number that is less than the number of electrode terminals operable for stimulation (e.g., five pulse generator outputs for sixteen electrodes), and thus reduces the number of coupling capacitors. In another embodiment, the present invention provides for a reduction in the number of coupling capacitors to a number that is less than the number of electrode terminals operable for stimulation. This approach allows for an increased number of pulse generator outputs (and channels/electrodes) without significantly increasing the number of coupling capacitors, or alternatively, allows for a reduction in the number of coupling capacitors for a given number of pulse generator outputs as compared to prior art systems.

The pulse generator outputs P1 thru Pn are coupled to a bank of coupling capacitors 202. In the embodiment shown, the coupling capacitors 202 include a plurality n of coupling capacitors. Each of the pulse generator outputs P1 thru Pn are coupled to a corresponding coupling capacitor C1 thru Cn, which in turn, is coupled to a plurality n of intermediate terminals (e.g., nodes, connection points, etc.) T1 through Tn. The term "terminal" may refer to any connection point or node. The intermediate terminals T1 thru Tn are coupled to the programmable switch array 204. The coupling capacitors C1 thru Cn may each include a single capacitor or multiple capacitors, and are typically greater than about 1 microFarad, and usually in the range of about 1-100 microFarad, and typically about 15-22 microFarad.

It will be understood by those skilled in the art that a "pulse generator output" may also include, or contemplate, a ground line, sometimes referred to as a can or case ground (in monopole operation). Such ground line may be coupled to one of the coupling capacitors C, or may be coupled to an electrode terminal without use of a coupling capacitor.

The programmable switch array 204 is programmed or controlled to selectively switch/couple one or more of the intermediate terminals T1 thru Tn to any one or more of a plurality y of electrode output terminals E1 thru Ey. Accordingly, the terminal T1 (and the pulse generator output P1) may be coupled to any number of the electrode output terminals E1 thru Ey, the terminal T2 (and the pulse generator output P2) may be coupled to any number of the electrode terminals E1 through Ey, and so on. In a typical configuration, the electrode terminals E1 thru En are thereafter coupled to one or more leads having a number of electrodes.

In the embodiment shown in FIG. 2, the implantable device 100 includes n number of pulse generator outputs and the same number n of coupling capacitors, while there exist y number of electrode output terminals (or electrodes), where y is greater than n.

The switch array 204 is shown controlled by the controller 201 (and/or pulse generator output circuit 200), but may be controlled by any other circuit or functionality as desired and provided within the device 100. The switch array 204 is constructed using mechanical, electromechanical or electrical switches or other switching devices, any combination thereof, or any other device known to those skilled in the art that includes switching functionality, and may further include solid-state switches (such as FET switches) or a MEMS device(s). The switch array 204 may be in the form of single or multiple integrated circuits (IC) or discrete components that are separate from the other elements/components of device 100. Alternatively, the switch array 204 may be fabricated as part of an IC that includes one or more other elements/components of the device 100, and/or may operate within one or more printed circuit board (PCB) structure(s).

In certain embodiments, switch array 204 is composed of nanowire switches. Nanowire switches can advantageously be employed in certain embodiments of the present invention due to their capacity to act as capacitors when placed in proximity to each other, and as switches when subjected to an applied voltage. Nanowires are comprised of various electrically conductive materials such as, for example, silver sulphide or platinum.

In one embodiment, the switch array 204 includes a plurality of 1-to-y demultiplexers (not shown), and more particularly, provides n number of 1-to-y demultiplexers. Such configuration provides programmability whereby each of the pulse generator outputs P1 thru Pn (and respectively terminals T1 thru Tn) are capable of being electrically coupled (switched) to any one of the electrode terminals E1 thru Ey. This generally provides a one-to-one correspondence (e.g., P1 to a one of E1 thru Ey, P2 to a one of E1 thru Ey, etc.).

In another embodiment, the switch array 204 includes one or more multiplexers, demultiplexers, decoders, multiposition switches and/or other discrete switches, or combination(s) thereof, (not shown) to provide a configuration that provides programmability whereby each of the pulse generator outputs P1 thru Pn (and respectively terminals T1 thru Tn) are capable of being electrically coupled (switched) to any one or more of the electrode terminals E1 thru Ey. In another embodiment, the switch array 204 may include y number of n-to-1 multiplexers (not shown) for such functionality. Other switching configurations are possible to provide the overall desired functionality whereby a given pulse generator output may be coupled to one, two or all of the electrode terminals E1 thru Ey.

Other configurations are possible, one of which is described below in reference to FIG. 6, that select specific pulse generator outputs P1 thru Pn for switching to a limited number or set of the electrode terminals E1 thru Ey. In other embodiments, the switch array 204 may include discrete switches, standard functional multiplexers and/or, demultiplexers, etc. or any combination thereof, as chosen to accomplish the desired functions taught herein. Additionally, it may be desirable to include functionality capable of switching two or more pulse generator outputs to a given electrode terminal E.

The implant device 100 further includes the power source 208 that provides power as needed for operation of the implant device 100 (and may include power regulation and control circuitry, not shown). The power source 208 will typically include a permanent (long-lasting) battery or a replenishable power source (by recharging, such as rechargeable battery or supercapacitor) for providing power. Recharging may occur wirelessly (e.g. RF, inductive, using a coil/antenna) via the power section 214 of the transmitter/receiver 210. In a configuration where the implantable device 100 does not have any appreciable power storage capabilities (receives and utilizes power directly from an external device), the power source 208 may be configured to include circuitry operable to control and regulate the power directly received from an external device via wireline or wireless (e.g., RF, inductive).

In certain embodiments of the present invention, power source 208 comprises a miniature battery that can be either rechargeable or permanent. Such batteries utilize various electrochemistries to generate electrical power. The various electrochemistries may use a variety of compounds, such as, for example, polymer electrolytes or lithium-ion electrolyes.

The transmitter/receiver 210 further includes a communications section 212 that provides communication capabilities with an external device to provide programmability and control (and monitoring) of the implant device 100, and further allows the implant device 100 to communicate with the external device.

Due to reliability and/or safety factors, it is desirable to prevent exposure of potential DC leakage current to the electrode output terminals (i.e., to the tissue being stimulated). When solid-state devices are utilized (or any other devices capable of leaking DC current) to function as the switch array 204, a sense circuit 216 is optionally provided that functions to sense whether any DC leakage is occurring with respect to the switch array. If the DC leakage exceeds a predetermined threshold (current or voltage), a signal is generated. In one embodiment, the sense circuit 216 senses the power supply line(s) to the switch array 204. If the supply (current or voltage) exceeds a predetermined threshold at a given time, the sense circuit generates a signal indicating an overcurrent (or overvoltage) condition, and then the switch array 204 and/or the implantable device 100 may be powered down. Generally, a switch array 202 in accordance with the present invention may consume a small amount of DC current in its static state (non-switching), eg., in the range of 0 to 500 nA. For illustrative purposes, when the sense circuit 216 detects a current of around one uA, then the array 204 and/or device 100 may be powered down for safety reasons. In other embodiments, the output nodes or other points/nodes of the switching array 204 or other included elements up to the lead connections may also be sensed.

Figure 1:
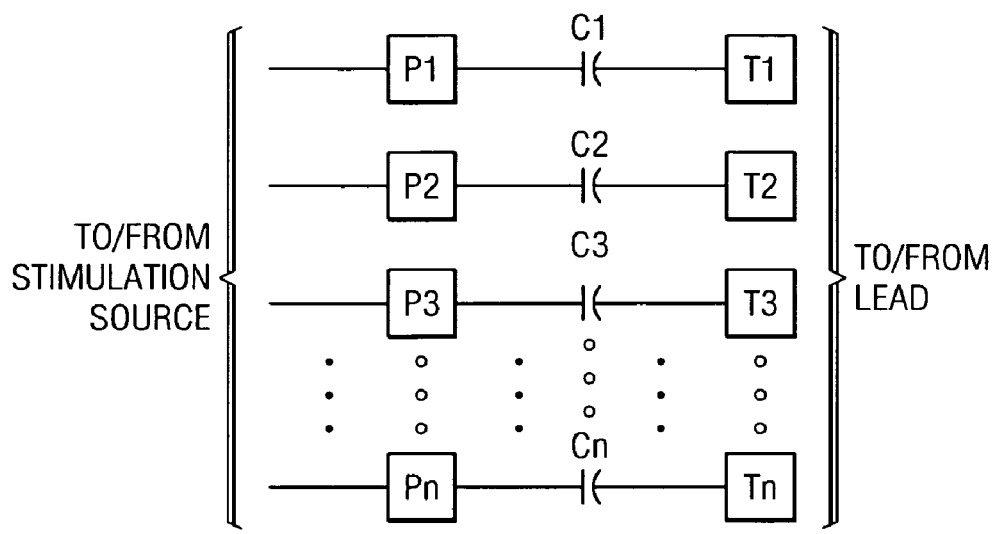
FIG. 1 illustrates a coupling capacitor configuration for a prior art implantable stimulation device.
Figure 3:
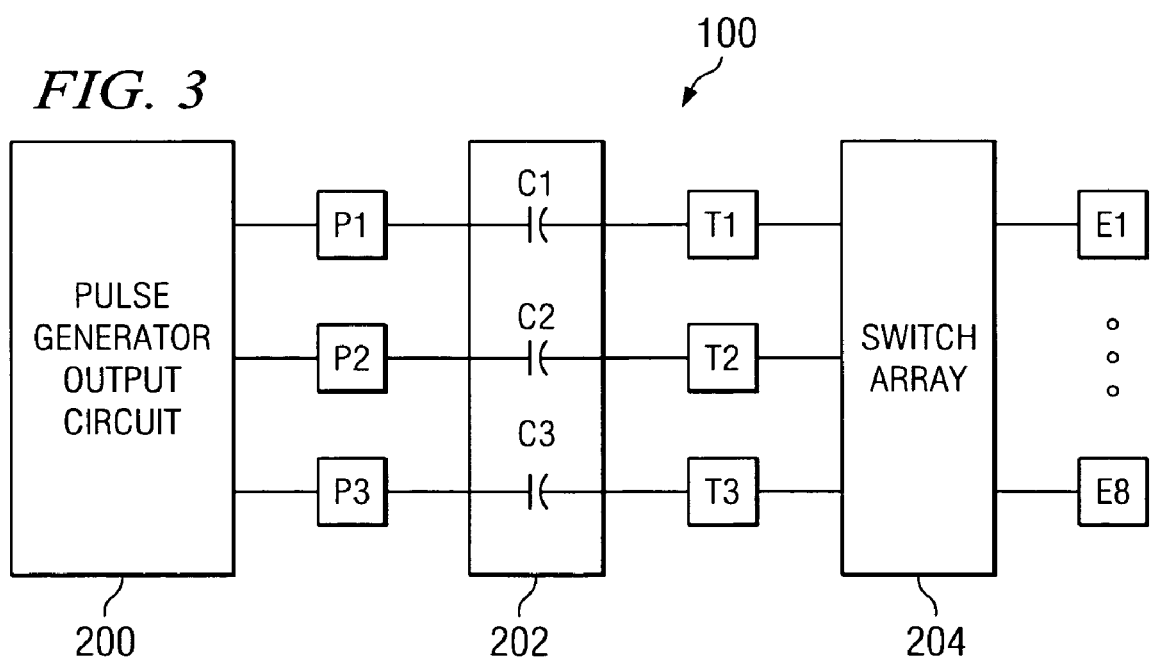
FIG. 3 illustrates one specific example of the implantable device shown in FIG. 2 configured with three pulse generator outputs operable for switching to one or more of eight possible electrode output terminals.

FIG. 3 illustrates a specific example of the relevant portions of the implantable device 100 shown in FIG. 2. The pulse generator output circuit 200 generates three pulse generator outputs, P1, P2 and P3 (generated from one or more sources) that are coupled, respectively, to coupling capacitors C1, C2 and C3. The terminals T1, T2 and T3 are coupled to the switch array 204 having eight electrode terminals, E1 thru E8. With reference to the configuration of device 100 shown in FIG. 2, the example shown in FIG. 3 illustrates n=3 and y=8. The three pulse generator outputs (via terminals T1 thru T3) are individually switched or selectively connected (or disconnected from), to one or more of the plurality (8) electrode terminals E1 thru E8. The switching is controlled by control signals generated from the pulse generator output circuit 200 and/or controller 201.

In this specific example, the switching array 204 may include eight 3-to-1 multiplexers, one for each terminal T1, T2, T3 (pulse generator outputs P1, P2, P3). The multiplexers may include, as described earlier, switches in the form of mechanical, electro-mechanical, or electrical switches. Alternatively, the switch array 204 may include discrete switching elements, and may further include decoding circuitry. Other switching array configurations are possible, as described above.

Figure 4:
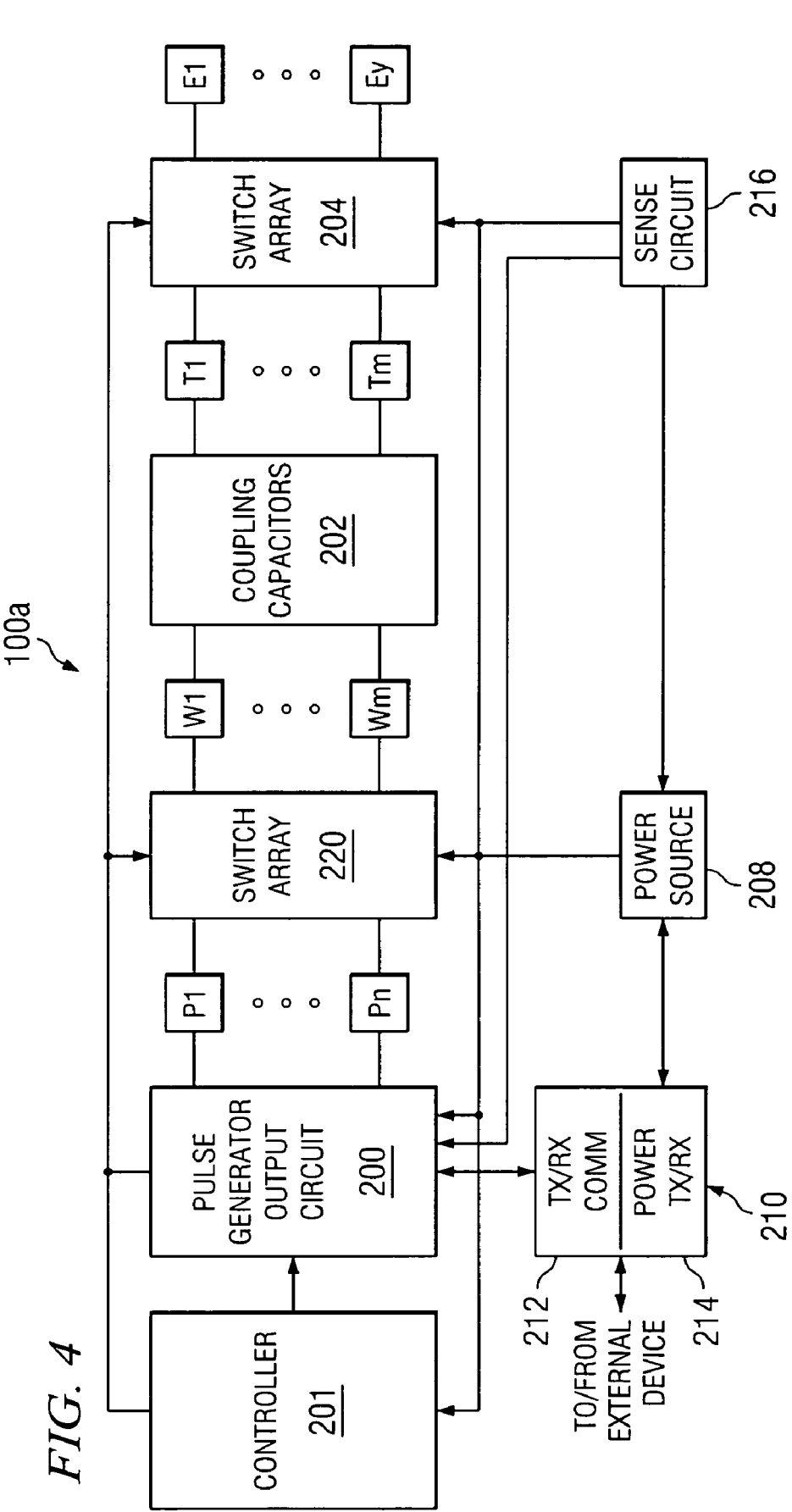
FIG. 4 is a block diagram illustrating another embodiment of an implantable device in accordance with the present invention.

Now referring to FIG. 4, there is shown another embodiment of an implantable device 100a of the present invention. The implantable device 100a is similar to the device 100 shown on FIG. 2, and further includes another programmable switch array 220.

The pulse generator output circuit 200 generates a plurality n of electrical signals via a plurality of separate and independently programmable corresponding terminals P1 thru Pn. The pulse generator outputs P1 thru Pn are coupled to the switch array 220. The switch array 220 includes a plurality m of switched output terminals W1 thru Wm. The plurality of switched output terminals W1 thru Wm (selected pulse generator outputs) are coupled to the bank of coupling capacitors 202. In the embodiment shown, the coupling capacitors 202 include a plurality m of coupling capacitors. Each of the switched output terminals W1 thru Wm are coupled to a corresponding coupling capacitor C1 thru Cm, which in turn, is coupled to a plurality m of intermediate terminals T1 through Tm. The intermediate terminals T1 thru Tn are coupled to the programmable switch array 204. The coupling capacitors C1 thru Cm may each include a single capacitor or multiple capacitors, and are typically on the order of 15 uF.

The programmable switch array 220 is programmed or controlled to selectively switch/couple one or more of the pulse generator outputs P1 thru Pn to any one or more of the plurality m of switched output terminals W1 thru Wm. Accordingly, the output pulse generator P1 may be coupled to any number of the switched output terminals W1 thru Wm, the output terminal P2 may be coupled to any number of the electrode output terminals W1 thru Wm, and so on. As such, selected pulse generator outputs P1 thru Pn are present at the switched output terminals.

In the embodiment shown in FIG. 4, the implantable device 100a includes n number of pulse generator outputs, m number of switched output terminals, the same number m of coupling capacitors, the same number m of intermediate terminals, and y number of electrode output terminals (or electrodes). In this embodiment, n is greater than m, and y is greater than m. Another embodiment further includes where n equals or is less than y.

The programmable switch array 204 operates similarly as described above with respect to FIG. 2. In a typical configuration, the electrode output terminals E1 thru Ey are thereafter coupled to one or more leads having a number of electrodes.

The embodiment shown in FIG. 4 can be utilized with existing prior art systems, with the inclusion of the two switch arrays 204, 220, and some switching control functions, which leads to the a beneficial reduction in the number of coupling capacitors without any change or substantial change to the pulse generator output circuit 200. For example, in a prior art system where the circuit 200 includes eight or sixteen pulse generator outputs (and eight or sixteen coupling capacitors), the switch array 220 operates effectively to allow a reduction in the number of outputs for coupling to the capacitors, thus reducing the number of needed coupling capacitors, without any substantial redesign or reconfiguration of the pulse generator output circuit 200.

As previously described, the pulse generator output(s) may originate from one or multiple source circuits, such as separate and independently controllable constant voltage source(s) or constant current source(s), or combination thereof.

In one embodiment, the switch array 220 includes a plurality of n-to-1 multiplexers (not shown), and more particularly, provides m number of such multiplexers. The switch array 204 includes a plurality of 1-to-y demultiplexers (not shown), and more particularly, provides y number of m-to-1 demultiplexers. Other embodiments and configurations are possible, as mentioned earlier, operable to provide switching of the pulse generator outputs in a one-to-one correspondence or a one-to-many correspondence (e.g., a given pulse generator output may be coupled to one, two or all of the electrode terminals E1 thru Ey).

Figure 5:
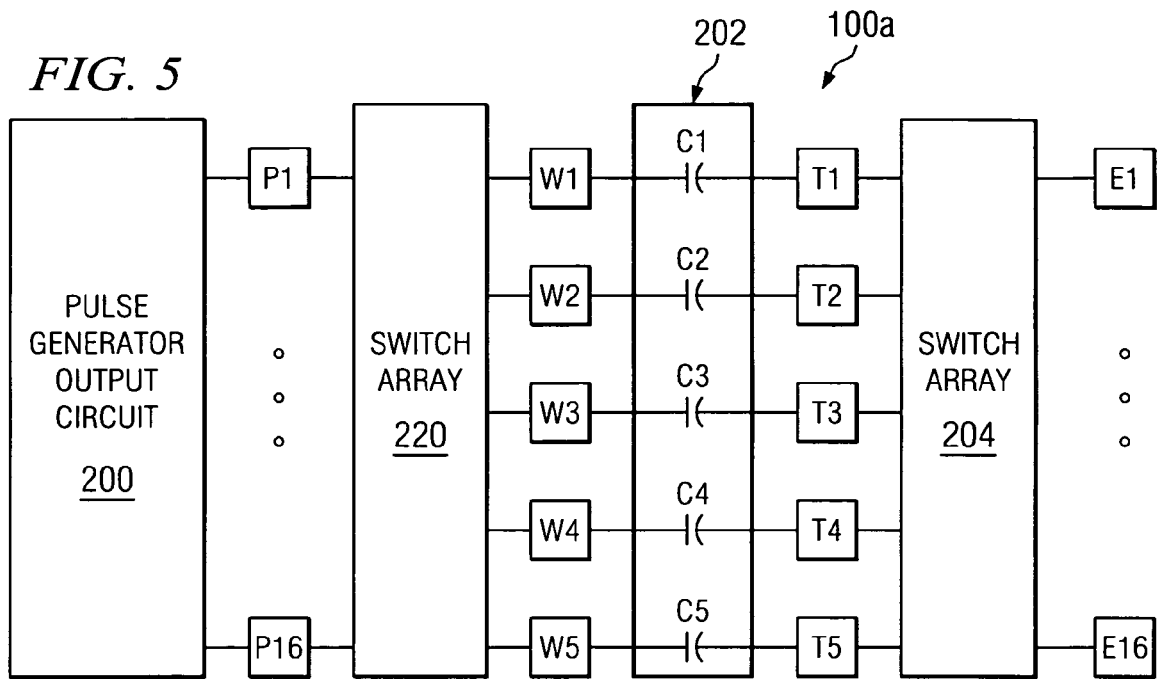
FIG. 5 illustrates one specific example of the implantable device shown in FIG. 4 configured with sixteen pulse generator outputs operable for switching to one or more of sixteen possible electrode output terminals.

FIG. 5 illustrates a specific example of the relevant portions of the implantable device 100a shown in FIG. 4. The pulse generator output circuit 200 generates sixteen pulse generator outputs, P1 thru P16 (generate from one or multiple sources) that are coupled, respectively, to the switch array 220. The switch array 220 receives P1 thru P16 and selectively switches one or more of the sixteen pulse generator outputs to one or more of the five switched array outputs W1, W2, W3, W4 and W5. The five switched array outputs W1 thru W5 are coupled to the coupling capacitors C1, C2, C3, C4 and C5. The terminals T1, T2, T3, T4 and T5 are coupled to the switch array 204 having sixteen electrode terminals, E1 thru E16.

With reference to the configuration of device 100a shown in FIG. 4, the example shown in FIG. 5 illustrates n=16, m=5, and y=16. One or more of the sixteen pulse generator outputs (via switched outputs W1 thru W5, and terminals T1 thru T5) are switched or selectively connected (or disconnected), to one or more of the plurality of electrode terminals E1 thru E16. The switching is controlled by control signals generated from the pulse generator output circuit 200 and/or controller 201.

In this specific example, the switching array 220 may include five 16-to-1 multiplexers (one for each switched output W1 thru W5), and the switching array 204 may include five 1-to-16 demultiplexers (one for each terminal T1 thru T5. As will be appreciated, other configurations (multiplexers, demultiplexers, decoders, discrete switches, and combinations of these) of the switching device may be utilized. The multiplexers and demultiplexers may include, as described earlier, switches in the form of mechanical, electro-mechanical, or electrical switches. Alternatively, the switch arrays 204, 220 may include discrete switching elements, and may further include decoding circuitry.

It will be appreciated that the control circuitry and control signals utilized to select which of the pulse generator outputs P1 thru P16 are active, at any given time, may be the same signals, or utilized to generate additional control signals, for switch control of the switch arrays 204, 220.

Figure 6A:
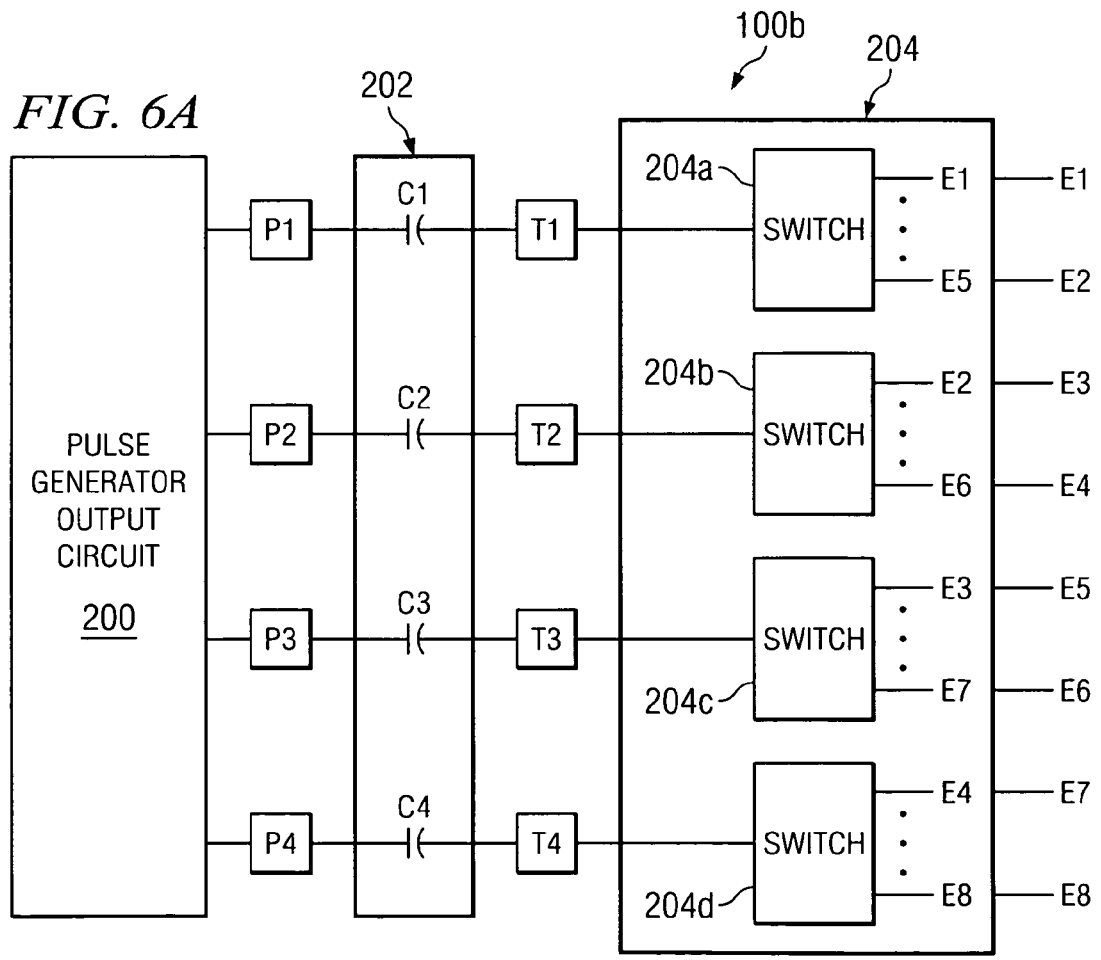
FIGS. 6A, 6B and 6C are block diagrams illustrating other embodiments of an implantable device in accordance with the present invention.
Figure 6B:
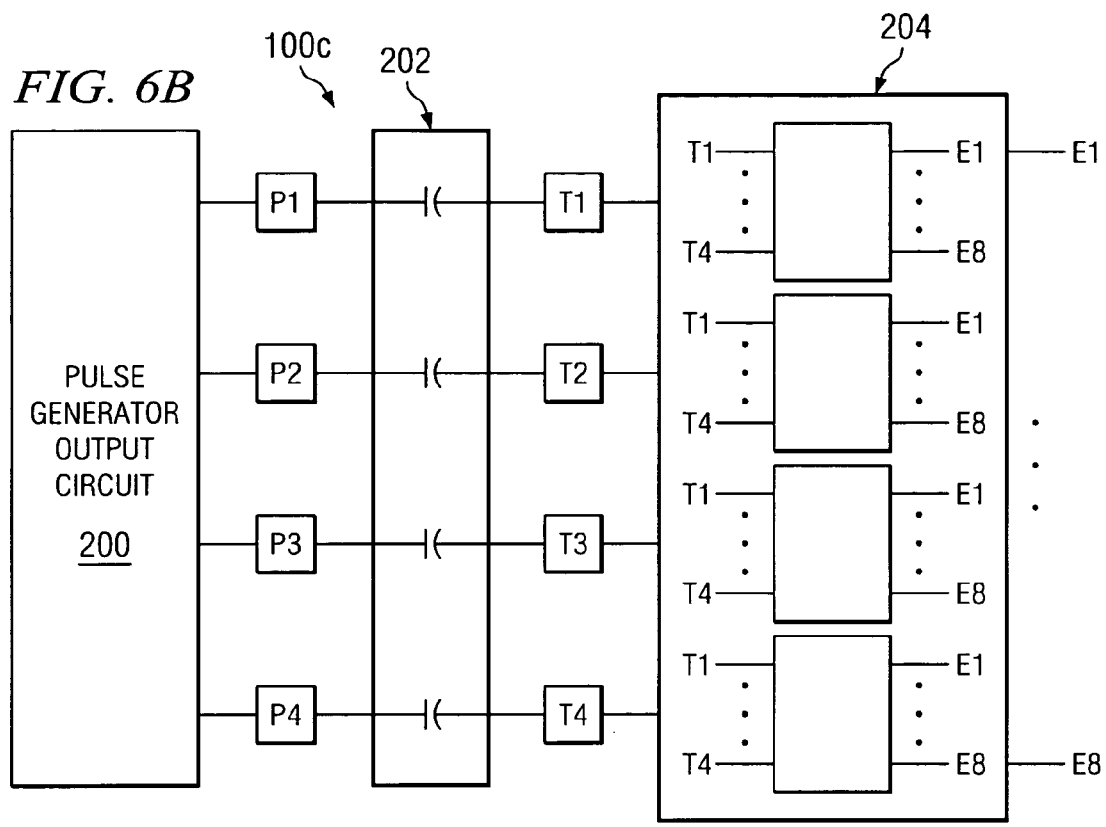
Figure 6C:
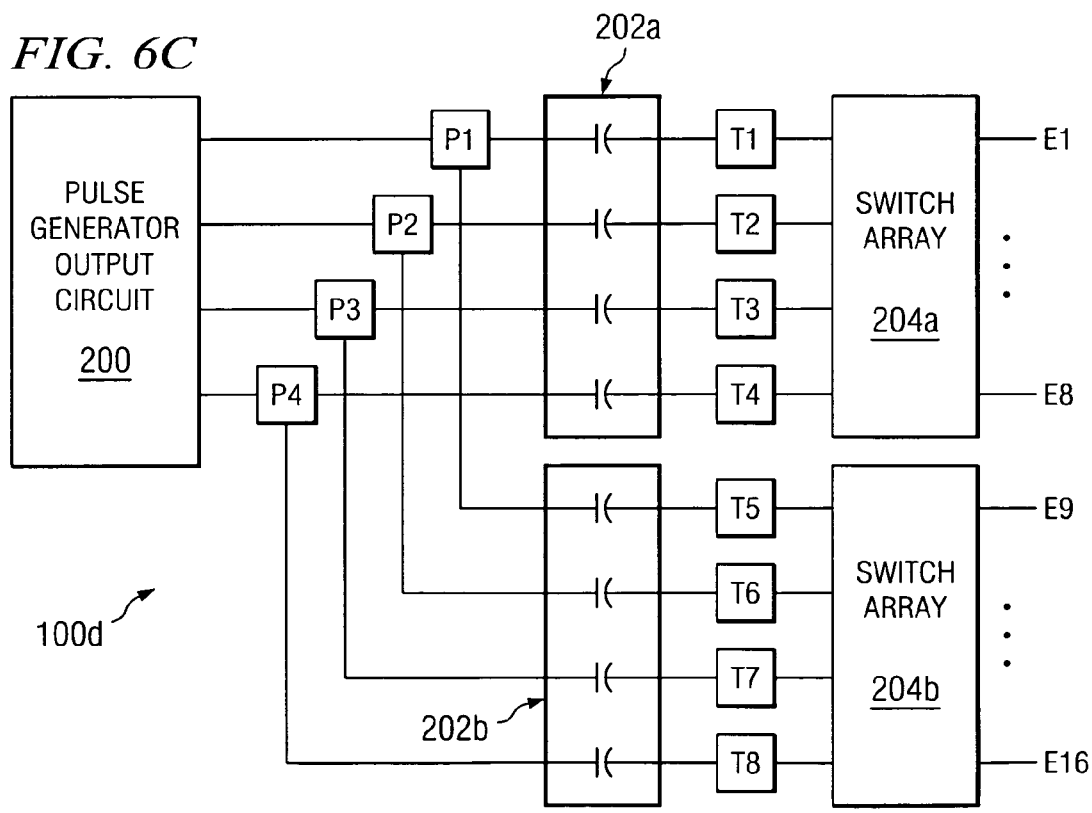

Now referring to FIGS. 6A, 6B and 6C, there are shown other embodiments of an implantable device 100b, 100c and 100d of the present invention.

The implantable device 100b in FIG. 6A is similar to the device 100 shown on FIG. 2 with the main difference being that each of the specific pulse generator outputs P1 thru P4 are switched to a limited number or subset of the electrode terminals E1 thru Ey. One advantage to this configuration is the reduction in the number of switches. Though this embodiment may not allow each output to be coupled to any of the electrode terminals concurrently, it still maintains some programmability while reducing the number/size of switching components, and provides for a one-to-one correspondence (i.e., each output may be coupled to one of the electrode terminals).

In this embodiment, when n number of pulse generator outputs and y number of electrode terminals are provided, the pulse generator output P1 is switchable to electrode terminals E1 thru E(y-(n-1)), while the pulse generator output P2 is switchable to electrode terminals E2 thru E(y-(n-2)), and so forth. One specific example is shown in FIG. 6, where n=4 and y=8.

The pulse generator outputs P1 thru P4 are coupled to the bank of coupling capacitors 202, as shown. The intermediate terminals T1 thru T4 are coupled to the programmable switch array 204.

As shown, the intermediate terminal T1 (and the pulse generator output P1) may be coupled to electrode terminals E1 thru E5, while the intermediate terminal T2 (and the pulse generator output P2) may be coupled to electrode terminals E2 thru E6, and so on. Alternatively, the terminal T1 may be coupled to electrode terminals E1 thru E8, terminal T2 coupled to terminals E2 thru E8, and so on (not shown). Or, terminal T1 may be coupled to terminals E1 through E5, terminal T2 coupled to terminals E1 through E6, and so on (not shown), all to provide additional flexibility in programming and interconnections. Other input-to-output interconnections may be provided, as desired.

In the embodiment shown in FIG. 6A, the switch array 204 includes switches for switching the terminals T1 thru T4 to the electrode terminals E1 thru E8, as shown. And in the specific example shown, the switch array includes four 1-to-5 demultiplexers (204a thru 204d), or equivalent circuitry. Alternatively, the switch array 204 in FIG. 6A may include n number of 1-to-y demultiplexers (particularly, five 1-to-8 demultiplexers) for one-to-one correspondence switching capability (one input to one of the outputs), or may include y number of n-to-1 multiplexers (particularly, eight 4-to-1 multiplexers) for one-to-many correspondence switching capability (one input to any one or more of the outputs).

Now referring to FIG. 6B, there is shown a more generic embodiment. The switching array 204 is shown in block diagram form with blocks (elements/circuitry) to provide different configurations and interconnections, such functioning to provide (1) one-to-one correspondence switching capability (one input to one of the outputs); (2) one-to-many correspondence switching capability (one input to any one or more of the outputs); and/or (3) many-to-many correspondence switching capability (any one or more input to any one or more of the output), or combination thereof. Alternative embodiments may include any number of pulse generator outputs Pn, and in one embodiment is configured with only two pulse generator outputs, P1 and P2.

Now referring to FIG. 6C, there is shown another embodiment of the implantable device 100d. The pulse generator outputs P1 thru P4, are each coupled to a plurality of coupling capacitor devices, 202a, 202b, as shown, to provide additional terminals T1 thru T8 which are switchable to a greater plurality of electrode terminals E1 thru E16, as described. The present invention may be scaled or cascaded in any fashion to provide greater flexibility, programmability and capacity.

As will be appreciated, an alternative embodiment to those described herein may alternatively provide the switch array 204 positioned on a lead, or intermediate device (between the lead and the implantable device), or particularly near the distal end of the lead. This would allow for a reduction in the number of conductors needed to provide electrical connection to the electrodes of the lead (for contact with the object). Moreover, the sense circuit 216 may be provided in the implantable device or in the lead.

It will be understood that the terms "terminal", "node" or "connection" as used herein should not be construed in any limiting manner, and may refer to any type of connection, node or other connection between two or more points or signals, whether mechanical or electrical, or internal or external to any integrated circuit or other discrete element(s).

Figure 7:
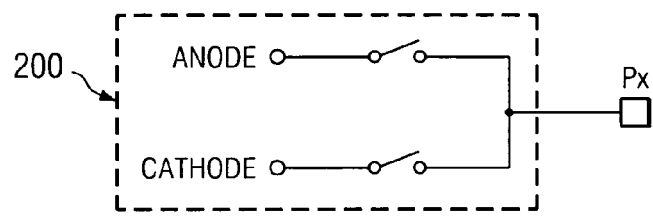
FIG. 7 illustrates the programmability of the pulse generator outputs to allow the outputs to function in one of three states (anode, cathode, or high impedance (tri-state)

Now turning to FIG. 7, there is shown a schematic illustrating a portion of the pulse generator circuit 200 functionally describing that the pulse generator outputs Pn are programmable and operable to function (active) in an anode or cathode mode (with sink or source capability). In addition, the outputs are capable of a high impedance state (i.e., off or tri-state), as described previously.

Figure 8:
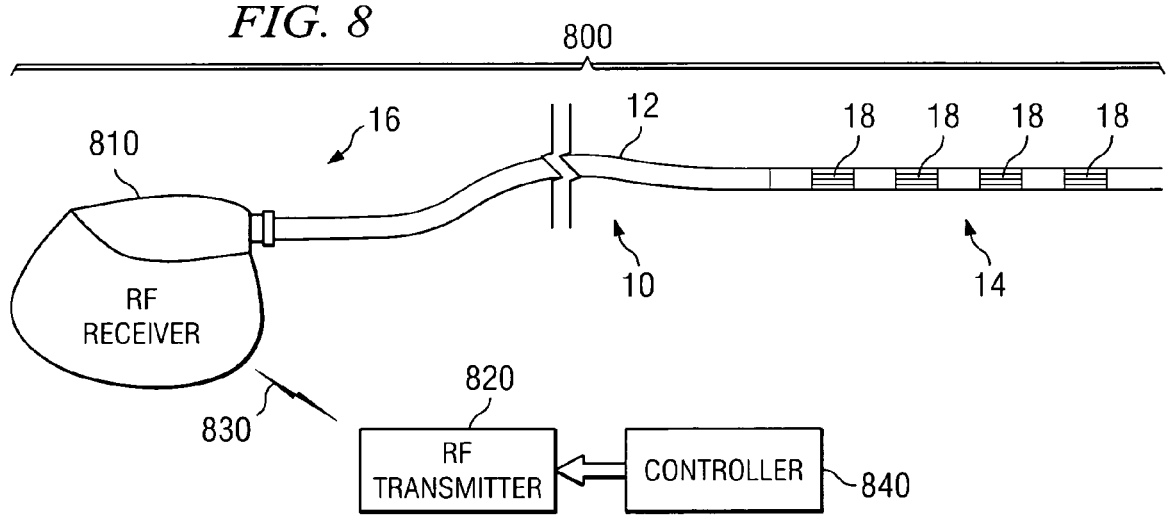
FIG. 8 illustrates one embodiment of a system for stimulation in accordance with the present invention.

With reference to FIG. 8, there is shown a stimulation system 800 in accordance with the present invention. The stimulation system 800 generates and applies a stimulus to a tissue or to a certain location of a body. In general terms, the system 800 includes an implantable pulse generator (IPG) 810 that provides a stimulation or energy source and a lead 10 for application of the stimulus. The lead 10 shown in FIG. 8 is described below.

The lead 10 includes a distal end 14 and a proximal end 16. The lead 10 includes a lead body 12 that extends from the distal end 14 to the proximal end 16. The distal end 14 of the lead 10 is shown including four electrodes 18. The proximal end 16 of the lead 10 includes four contacts or ring contacts (not shown) that form a lead connector. The lead 10 generally includes one or more conductors (not shown) extending a substantial portion of the lead 10 to electrically connect the contacts to respective electrodes 18. An optional lumen (not shown) may extend through the lead 10 and may be used for different purposes, including the delivery of chemicals or drugs.

As will be appreciated, any number of conductors and electrodes may be utilized, as desired. For purposes of illustration only, the lead 10 is shown with four electrodes. In addition, other types, configurations and shapes of electrodes (and lead connectors) as known to those skilled in the art may be used, as desired.

Typically, the lead body 12 is a structure having a round cross-section. Alternatively, the cross-section of the lead body 12 may be configured in any number of cross-sectional shapes appropriate for the specific application. The following description generally refers to a round cross-sectional shape for the lead body 12 for illustrative purposes only. The lead body 12 generally includes a lead body insulator configured to insulate the conductors and present a biocompatible external surface to the body tissue.

The lead body insulator is formed of insulating material typically selected based upon biocompatibility, biostability and durability for the particular application. The insulator material may be silicone, polyurethane, polyethylene, polyamide, polyvinylchloride, PTFT, EFTE, or other suitable materials known to those skilled in the art. Alloys or blends of these materials may also be formulated to control the relative flexibility, torqueability, and pushability of the lead 10. Depending on the particular application, the diameter of the lead body 12 may be any size, though a smaller size is more desirable for neurological and myocardial mapping/ablation leads and neuromodulation and stimulation leads.

The conductors (not shown) may take the form of solid wires, drawn-filled-tube (DFT), drawn-brazed-strand (DBS), stranded wires or cables, ribbons conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. The number, size, and composition of the conductors will depend on the particular application for the lead 10, as well as the number of electrodes.

The conductors may be configured along the lead body 12 in a straight orientation or spirally or helically wound about the optional lumen or center of the lead body 12. The conductors are typically insulated from the optional lumen, from each other, and from the external surface of the lead 10 by insulative material. The insulative material may be of a single composition, or multiple layers of the same or different materials.

In one embodiment, the lead 10 is generally configured to transmit one or more electrical signals from a source for application at, or proximate to, a spinal nerve or peripheral nerve, or other tissue.

The electrodes are typically made of a conductive material such as platinum, gold, silver, platinum-iridium, stainless steel, MP35N, or other conductive materials, metals or alloys known to those skilled in the art. The size of the electrodes is generally chosen based upon the desired application.

As shown in FIG. 8, the stimulation system 800 includes the lead 10 that is coupled to the stimulation implantable pulse generator (IPG) 810.

In one embodiment, the IPG 810 may include a self-contained implantable pulse generator (SCIPG) or externally-powered implantable pulse generator (EP1PG). As used herein, an SCIPG is an IPG having an implanted power source, such as a long-lasting or rechargeable battery. An EP1PG is an IPG that receives at least some of its operating power from an external power transmitter, preferably in the form of a wireless signal (RF, inductive, etc.). As is known in the art, the implantable pulse generator (IPG) is capable of being implanted within the body (not shown) that receives electrical stimulation from the IPG 810.

An external transmitter 820 (or programmer/controller) may be provided to control and/or program the IPG 810 via a communications link 830 between the IPG 810 and the external programmer/controller. When in the form of an SCIPG, the transmitter 820 may also provide power to the IPG 810. A separate controller 840 may be provided which controls/programs the transmitter 820. In some embodiments, the controller 840, and collectively the transmitter 820 and controller 840 are referred to as an external patient controller/programmer (EPP).

As shown in FIG. 8, the stimulation system 800 includes the lead 10 that is coupled to the IPG 810. The IPG 810 typically includes the transmitter/receiver 214 (shown in FIG. 2). Communication/power signals are represented in FIG. 8 by the wireless link symbol 830. The transmitter 820 and the controller 840 are located outside of the body that is to receive electrical stimulation from the IPG 810. A user of the IPG 810 may use the transmitter 820 and/or controller 840 to provide control signals for the operation of the IPG 810. The controller 840 provides control signals to the transmitter 820. The transmitter 820 transmits the control signals (and optionally power) to the receiver in the IPG 810, and the IPG 810 responds to the control signals to vary the signal parameters of the electrical signals that are transmitted through lead 10 to the stimulation site.

As will be appreciated, the contact electrodes are not visible in FIG. 8 because the contact electrodes are situated within a receptacle (not shown) of the IPG 810. The contact electrodes electrically connect to a pulse generator circuit within the IPG 810. The IPG 810 generates and sends electrical signals via the lead 10 to the electrodes 18. Understandably, the electrodes 18 are located at a stimulation site (not shown) within the body that is to receive electrical stimulation from the electrical signals. A stimulation site may be, for example, adjacent to one or more nerves in the central nervous system (e.g., spinal cord). The IPG 810 is capable of controlling the electrical signals by varying signal parameters (e.g., intensity, duration, frequency) in response to control signals that are provided to the IPG 810.

It may be advantageous to set forth definitions of certain words and phrases that may be used within this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, such a device may be implemented in hardware, firmware or software, or some combination of at least two of the same. It should be noted that the functionality associated with any particular controller may be centralized or distributed, whether locally or remotely. The term "couple" or "connect" refers to any direct or indirect connection between two or more components, unless specifically noted that a direct coupling or direct connection is present.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An implantable pulse generator for generating electrical pulses for stimulation of tissue of a patient, comprising:
   pulse generating circuitry for generating electrical pulses;
   a plurality of capacitors for coupling electrical pulses from the pulse generating circuitry for output to the patient;
   a plurality of electrode output terminals with each electrode output terminals adapted to be electrically connected directly to a respective terminal of a stimulation lead, the plurality of capacitors being disposed between the pulse generating circuitry and the plurality of electrode output terminals;
   a first programmable switching device disposed between the plurality of capacitors and respective outputs of the pulse generating circuitry; and
   a second programmable switching device for selectively establishing electrical connections between each capacitor of the plurality of capacitors and one or more electrode output terminals of the plurality of electrode output terminals, wherein (i) the second programmable switching device is disposed between the plurality of capacitors and the plurality of electrode output terminals, (ii) the number of electrode output terminals of the plurality of electrode output terminals is greater than the number of capacitors of the plurality of capacitors, and (iii) the second programmable switching device comprises a plurality of de-multiplexers with the outputs of each de-multiplexer coupled to a respective distinct subset of the plurality of electrode output terminals;
   wherein at least two of the de-multiplexers of the plurality of de-multiplexers comprise at least one electrode output terminal in common between connections to their respective subsets of electrode output terminals.

2. The implantable pulse generator of claim 1 further comprising:
a sensing circuit for sensing DC leakage current through the second programmable switching device and generating a signal when a predetermined threshold is exceeded.

3. The implantable pulse generator of claim 1 wherein each capacitor of the plurality of capacitors is coupled to multiple de-multiplexers of the plurality of de-multiplexers.

4. The implantable pulse generator of claim 1 further comprising:
a controller for controlling the implantable pulse generator, the controller controlling the first and second programmable switching devices such that, during stimulation pulse delivery, each electrode output terminal of the plurality of electrode output terminals conducting current of a pulse is coupled to a unique capacitor of the plurality of capacitors.

5. A system for electrically stimulating tissue of a patient, the system comprising:
a stimulation lead comprising a first plurality of electrical contacts on a proximal end of the stimulation lead and a second plurality of electrical contacts on a distal end of the stimulation lead; and
an implantable pulse generator for generating electrical pulses for stimulation of tissue of a patient, comprising:
pulse generating circuitry for generating electrical pulses;
a plurality of capacitors for coupling electrical pulses from the pulse generating circuitry for output to the patient;
a plurality of electrode output terminals with each electrode output terminals adapted to be electrically connected directly to a respective terminal of a stimulation lead, the plurality of capacitors being disposed between the pulse generating circuitry and the plurality of electrode output terminal;
a first programmable switching device disposed between the plurality of capacitors and respective outputs of the pulse generating circuitry; and
a second programmable switching device for selectively establishing electrical connections between each capacitor of the plurality of capacitors and one or more electrode output terminals of the plurality of electrode output terminals, wherein (i) the second programmable switching device is disposed between the plurality of capacitors and the plurality of electrode output terminals, (ii) the number of electrode output terminals of the plurality of electrode output terminals is greater than the number of capacitors of the plurality of capacitors, and (iii) the second programmable switching device comprises a plurality of de-multiplexers with the outputs of each de-multiplexer coupled to a respective distinct subset of the plurality of electrode output terminals;
wherein each capacitor of the plurality of capacitors is coupled to multiple de-multiplexers of the plurality of de-multiplexers.

6. The system of claim 5 wherein the implantable pulse generator further comprises:
a sensing circuit for sensing DC leakage current through the second programmable switching device and generating a signal when a predetermined threshold is exceeded.

7. The system of claim 5 wherein at least two of the de-multiplexers of the plurality of de-multiplexers comprise at least one electrode output terminal in common between connections to their respective subsets of electrode output terminals.

8. The system of claim 5 wherein the implantable pulse generator further comprises:
a controller for controlling the implantable pulse generator, the controller controlling the first and second programmable switching devices such that, during stimulation pulse delivery, each electrode output terminal of the plurality of electrode output terminals conducting current of a pulse is coupled to a unique capacitor of the plurality of capacitors.

* * * * *